(12) United States Patent
Mr

(10) Patent No.: US 10,261,061 B2
(45) Date of Patent: Apr. 16, 2019

(54) SYSTEM AND METHOD FOR BENCHMARKING, DETERMINING HEALTH INDICATOR, AND PREDICTIVE ANALYSIS OF GAS DATA

(71) Applicant: Honeywell International Inc., Morris Plains, NJ (US)

(72) Inventor: Gowrisankar Mr, Bangalore (IN)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 15/749,294

(22) PCT Filed: Jul. 29, 2016

(86) PCT No.: PCT/US2016/044624
§ 371 (c)(1),
(2) Date: Jan. 31, 2018

(87) PCT Pub. No.: WO2017/023723
PCT Pub. Date: Feb. 9, 2017

(65) Prior Publication Data
US 2018/0231516 A1    Aug. 16, 2018

(30) Foreign Application Priority Data
Aug. 6, 2015   (IN) .................. 4111/CHE/2015

(51) Int. Cl.
G08B 17/10     (2006.01)
G01N 33/00     (2006.01)
(Continued)

(52) U.S. Cl.
CPC ......... *G01N 33/0075* (2013.01); *G08B 21/14* (2013.01); *G08B 29/04* (2013.01)

(58) Field of Classification Search
CPC ........ F24F 11/30; F24F 2110/10; F24F 11/47; F24F 2110/70; F24F 2110/72;
(Continued)

(56) References Cited

U.S. PATENT DOCUMENTS 6,157,033 A * 12/2000 Chudnovsky ........... G01M 3/38
250/338.5
7,378,954 B2   5/2008 Wendt
(Continued)

FOREIGN PATENT DOCUMENTS

| EP | 3332250 A1 | 6/2018 |
|---|---|---|
| WO | 02063294 A2 | 8/2002 |
| WO | 2017023723 A1 | 2/2017 |

OTHER PUBLICATIONS

International Application No. PCT/US2016/044624, International Search Report, dated Oct. 7, 2016, 3 pages.
(Continued)

*Primary Examiner* — Daniel Previl
(74) *Attorney, Agent, or Firm* — Wick Phillips Gould & Martin, LLP

(57) ABSTRACT

Embodiments relate generally to systems and methods for improving the safety of work areas, especially in industries where there is a high probability of exposure to hazardous gases. The system may comprise an Intelligence System, wherein the system may generate a gas health indicator (GHI) value using quantified data received from a plurality of gas detectors within the workplace. This GHI may be used to compare sites within a workplace and suggest improvements, as well as predicting risk levels for areas of the workplace.

20 Claims, 2 Drawing Sheets

(51) Int. Cl.
*G08B 21/14* (2006.01)
*G08B 29/04* (2006.01)

(58) Field of Classification Search
CPC ............... F24F 2110/50; F24F 11/0017; F24F 11/0012; F24F 11/62; F24F 2011/0094; G05B 23/0235; G06Q 10/10; G06Q 30/0601; G06Q 40/06
USPC ......... 340/632, 540, 628, 691.4, 661, 691.6, 340/692, 687, 5.1, 815.79, 384.71, 393.4
See application file for complete search history.

(56) References Cited

U.S. PATENT DOCUMENTS

| | | | |
|---|---|---|---|
| 8,060,341 B2 | 11/2011 | Fluegge et al. | |
| 8,166,551 B2 | 4/2012 | King | |
| 2004/0089081 A1* | 5/2004 | Kretzschmar | G08B 17/10 73/866.1 |
| 2005/0104737 A1 | 5/2005 | Woodward | |
| 2006/0191341 A1* | 8/2006 | Olesen | G01M 3/243 73/592 |
| 2009/0312883 A1* | 12/2009 | Myllymaki | H02J 3/14 700/293 |
| 2011/0071963 A1 | 3/2011 | Piovesan et al. | |
| 2015/0106033 A1* | 4/2015 | Beerndt | G01N 33/0073 702/24 |
| 2015/0219609 A1* | 8/2015 | Soundarrajan | G01N 33/0006 702/104 |

OTHER PUBLICATIONS

International Application No. PCT/US2016/044624, Written Opinion of the International Searching Authority, dated Oct. 7, 2016, 6 pages.
International Application No. PCT/US2016/044624, International Preliminary Report on Patentability, dated Feb. 6, 2018, 7 pages.
Europe Patent Application No. 16753510.3, Communication pursuant to Rules 161(1) and 162 EPC, dated Mar. 13, 2018, 3 pages.
Europe Patent Application No. 16753510.3, Examination Report, dated Jan. 17, 2019, 8 pages.

* cited by examiner

SYSTEM AND METHOD FOR BENCHMARKING, DETERMINING HEALTH INDICATOR, AND PREDICTIVE ANALYSIS OF GAS DATA

CROSS-REFERENCE TO RELATED APPLICATIONS

The present application claims priority to and is the National Stage of International Application No. PCT/US2016/044624 filed on Jul. 29, 2016 and entitled "System and Method for Benchmarking, Determining Health Indicator, And Predictive Analysis of Gas Data" which claims priority to foreign Indian Provisional Patent Application Serial. No. 411/CHE/2015, filed on Aug. 6, 2015 with the Government of India Patent Office and entitled "System and Method for Benchmarking, Determining Health Indicator, And Predictive Analysis of Gas Data," both of which are incorporated herein by reference in their entirety.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Gas detectors are widely used to ensure the safety of workers in potentially hazardous environments. Data collected from gas detectors may be used to indicate the safety level of a worksite. Large numbers of workers within the worksite may carry gas detectors with them as they work. Also, maintenance checks and testing of the gas detectors may be performed regularly to ensure that the gas detectors are working properly.

SUMMARY

Aspects of the disclosure may include embodiments of a method for determining a safety benchmark for a workplace comprising receiving alarm data from a plurality of gas detectors within the workplace; receiving test data from the plurality of gas detectors within the workplace; receiving maintenance data from the plurality of gas detectors within the workplace; determining a first quantified parameter for the alarm data; determining a second quantified parameter for the test data; determining a third quantified parameter for the maintenance data; calculating a gas health indicator (GHI) using the quantified parameters; comparing the GHIs for multiple sites within the workplace; and generating suggested improvements for the workplace based on the GHI and the data used to determine the GHI, and the comparison with other sites within the workplace. In some embodiments, the GHI is calculated using the following equation: GHI=(Alarm data*A)+(Test data*B)+(Maintenance data*C), wherein A, B, and C are weighted variables. In some embodiments, the GHI is calculated using the following equation: GHI=(Alarm data*6)+(Test data*3)+(Maintenance data*1). In some embodiments, the alarm data comprises a normalized score that takes into account all of the alarm events that happen in an interval of time per the total number of gas detectors in use. In some embodiments, the test data comprises a normalized score that takes into account all of the test failures that happen in an interval of time per total gas detectors in operation. In some embodiments, the maintenance data comprises a normalized score that takes into account all of the maintenance failures that happen in an interval of time per the total number of gas detectors in use. In some embodiments, alarm data comprises panic alarms, danger alarms, warning alarms, false alarms, short term exposure limit (STEL) alarms, and time weighted average (TWA) alarms. In some embodiments, test data comprises using a gas detector with a fault and includes one or more of the following indications: Old Unit erasable programmable read-only memory (EPROM), Old Sensor EPROM, Low battery, Expired Sensor, and Damaged Sensor. In some embodiments, maintenance data comprises one or more of the following indications: Bump failed devices, Calibration failed devices, Calibration due devices, Zero Calibration test, Fresh Air test, Span test, Audio test (Peak and Minimum), and Vibrating Alarm test (when vibrator installed). In some embodiments, the method may further comprise predicting a risk level for a site based on the previously analyzed data, the GHI for the site, and the GHI for other sites in the workplace.

Additional aspects of the disclosure may include embodiments of a method for determining a safety benchmark for a workplace comprising receiving gas detector data from a plurality of gas detectors within the workplace; determining a first quantified parameter based on the received data; determining a second quantified parameter based on the received data; determining a third quantified parameter based on the received data; calculating a gas health indicator (GHI) using the quantified parameters using the following equation: GHI=(first quantified parameter*A)+(second quantified parameter*B)+(third quantified parameter*C), wherein A, B, and C are weighted variables; comparing the GHIs for multiple sites within the workplace; and generating suggested improvements for the workplace based on the GHI and the data used to determine the GHI, and the comparison with other sites within the workplace.

In some embodiments, the first quantified parameter comprises alarm data and comprises a normalized score that takes into account all of the alarm events that happen in an interval of time per the total number of gas detectors in use. In some embodiments, the second quantified parameter comprises test data and comprises a normalized score that takes into account all of the test failures that happen in an interval of time per total gas detectors in operation. In some embodiments, the third quantified parameter comprises maintenance data and comprises a normalized score that takes into account all of the maintenance failures that happen in an interval of time per the total number of gas detectors in use. In some embodiments, A is greater than B, and wherein B is greater than C.

Other aspects of the disclosure may include embodiments of a method for determining a safety benchmark for a workplace comprising receiving alarm data from a plurality of gas detectors within the workplace; receiving test data from the plurality of gas detectors within the workplace; receiving maintenance data from the plurality of gas detectors within the workplace; determining a first quantified parameter for the alarm data; determining a second quantified parameter for the test data; determining a third quantified parameter for the maintenance data; calculating a gas health indicator (GHI) using the quantified parameters using the following equation: GHI=(first quantified parameter*A)+(second quantified parameter*B)+(third quantified parameter*C), wherein A, B, and C are weighted variables; comparing the GHIs for multiple sites within the workplace; generating suggested improvements for the workplace based on the GHI and the data used to determine the GHI, and the comparison with other sites within the workplace; and predicting a risk level for a site based on the previously analyzed data, the GHI for the site, and the GHI for other sites in the workplace.

In some embodiments, the alarm data comprises a normalized score that takes into account all of the alarm events that happen in an interval of time per the total number of gas detectors in use. In some embodiments, the test data comprises a normalized score that takes into account all of the test failures that happen in an interval of time per total gas detectors in operation. In some embodiments, the maintenance data comprises a normalized score that takes into account all of the maintenance failures that happen in an interval of time per the total number of gas detectors in use. In some embodiments, the method may further comprise identifying and removing faulty data from the calculation.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1:
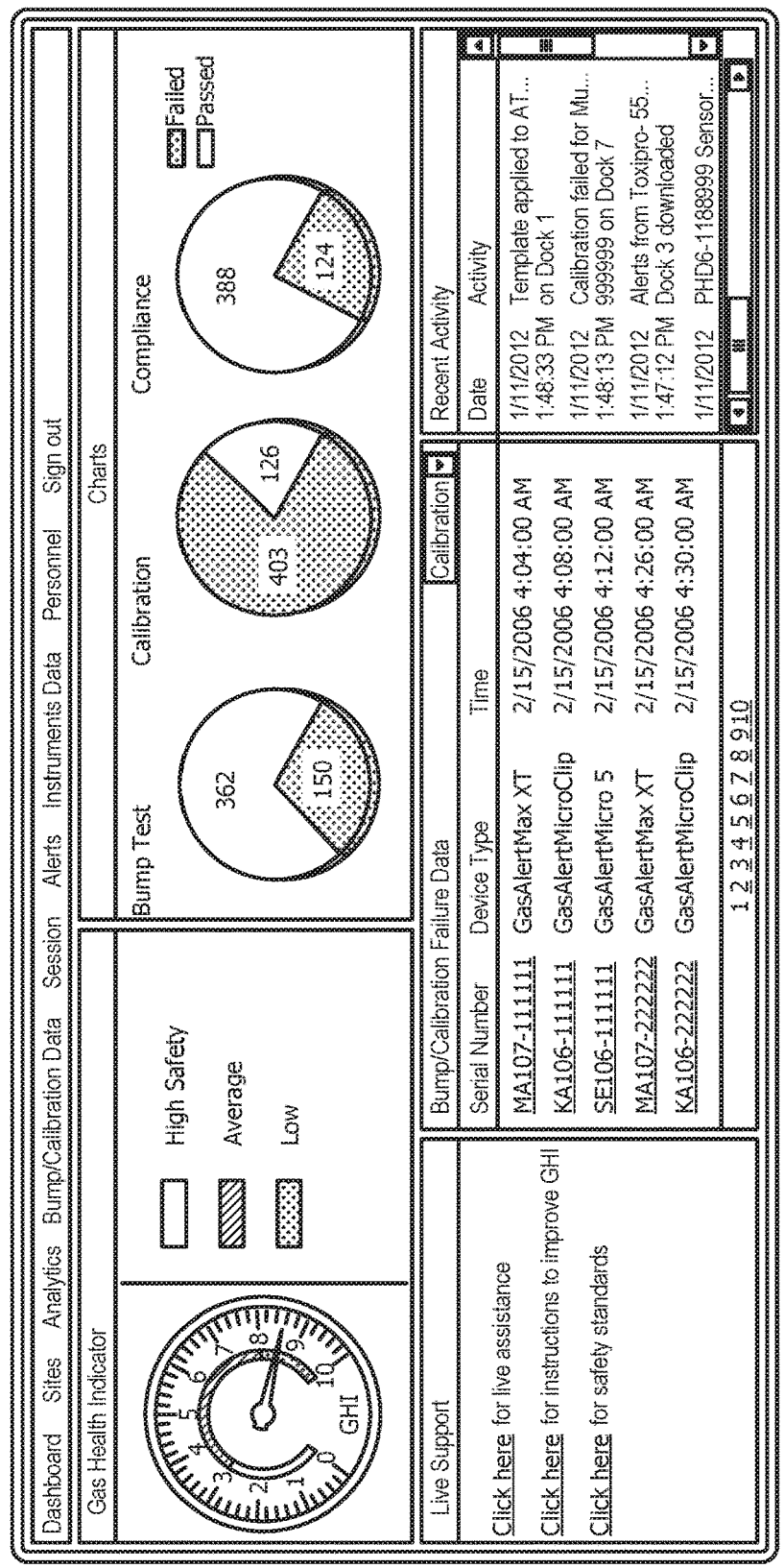
FIG. 1 illustrates a dashboard for display of test results and analyzed data.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Embodiments of the disclosure include systems and methods for improving the safety of work areas, especially in industries where there is a high probability of exposure to hazardous gases. The system may comprise an Intelligence System, wherein the system may provide (or generate) reports on testing of gas detectors (calibration and bump testing) as well as exposure data.

A workplace may employ a plurality of portable gas detectors, worn by workers in the workplace, to monitor gas exposure. The gas detectors may be equipped to detect the identity and levels of gases in the environment the user is working in. In some cases, exposure levels over a period of time may be limited to prevent overexposure to a user, wherein the gas detector may alert the user when a limit has been reached or exceeded. The gas detectors may be capable of monitoring one or more types of gases. Gas detectors may also be tested using bump testing, calibration testing, and maintenance testing, for example. These test results may be monitored and collected.

Typically, systems do not provide benchmarked results from multiple areas in a workplace, multiple workplaces, for comparison. The current solution provides a method for determining a Gas Health Indicator (GHI), which would benchmark safety information within a workplace with respect to gas detection (and exposure). The GHI may also be applied within similar areas across the workplace to compare the various areas (or sites) within the workplace. Even if the sites contain different gas concerns, such as different types of gases, different levels of exposure, etc., the benchmarked value may be used to compare the sites. By comparing the GHI across different areas of a workplace, possible improvements could be determined for each area based on areas with better a GHI. Collection of data alone can provide information about the risks in each area of a workplace, but the described method and system for generating a benchmark may provide a way to rate safety comparatively across a workplace, which would be helpful in determining improvements that may be implemented in various areas of a workplace. Additionally, multiple workplaces may be compared using an average GHI for each workplace.

A GHI may be calculated in intervals of time, wherein a specific area (or site) may have a GHI at a particular point in time. The GHIs determined at each time interval may be averaged to produce a daily GHI, a weekly GHI, a monthly GHI, etc. Additionally, the GHIs for multiple areas of a workplace may be averaged to determine a total GHI for the workplace In some embodiments, the GHI may be a number between 1 and 10, while in other embodiments, the minimum and maximum values may be different. Because the GHI is determined using failure data (alarms, test failures, maintenance failures), in some embodiments, a low GHI may indicate a high safety level, and therefore sites that the lowest GHI number could be regarded as the "High Safety Zone." Similarly, a high GHI may indicate a low safety level, and the sites with highest GHI could be termed "Critical or Low Safety Zone." The overall organization safety can be quantified by calculating an Overall GHI which is a simple average of the entire individual site's GHI.

In some embodiments, a maximum GHI may be identified, wherein it may be considered unacceptable for a site to have a GHI value high that the maximum GHI. If the maximum GHI is exceeded, steps may be taking to improve the quality of the gas sensors, reduce the amount of gas exposure, and other improvements that may decrease the calculated GHI for a site. These changes may be suggested by the system after analyzing the collected data, wherein the system may determine which steps could be taken to decrease the GHI score.

In some embodiments, the Intelligence System may analyze data related to the "High Safety Zone" and relate it with other sites to generate recommendations for the best practices to improve an individual site's GHI. By analyzing a site with a high GHI, other sites may be improved by implements practices similar to those of the "High Safety Zone." In existing solutions, a safety manager may be able to receive reports of testing, exposure, and other data from gas detectors, but there is no way to normalize data across a workplace to draw conclusions and comparisons between the areas. By using the information to determine a GHI for each area, the safety of the workplace may be improved.

The following equation shows an exemplary method of determining a GHI value, wherein different factors may be weighted differently. For example, in the equation below, variables A, B, and C may all have different values, thereby weighting the parameters differently. In some embodiments, one or more of the variables may be equal.

$$GHI = (\text{Alarm data} * A) + (\text{Test data} * B) + (\text{Maintenance data} * C)$$

The equation includes three parameters, each multiplied by a weight number. The first parameter, "alarm data," may be a normalized score that takes into account all of the alarm events that happen in an interval of time per the total number of gas detectors in use. The alarm data parameter may yield a fraction that is then multiplied by the weight number A. The second parameter, "test data," may comprise a normalized score that takes into account all of the test failures that happen in an interval of time per total gas detectors in operation. The test data parameter may yield a fraction that is then multiplied by the weight number B. The third parameter, "maintenance data," may comprise a normalized score that takes into account all of the maintenance failures that happen in an interval of time per the total number of gas detectors in use. The maintenance data parameter may yield a fraction that is then multiplied by the weight number C.

In one embodiment, the weight numbers may be valued as follows: A=6, B=3, C=1, wherein the weight numbers add to a total of 10, such that the highest GHI value possible is 10. In this case, A is weighted more because the alarm data indicates actual hazardous gas level events. B and C may be weighted less because they indicate events where there potentially could have been hazardous gas levels that were not detected by the gas detector, because the gas detector indicated testing (bump or calibration) or maintenance failure.

As an example, alarm data may include panic alarms, danger alarms, warning alarms, false alarms, short term exposure limit (STEL) alarms, and time weighted average (TWA) alarms. In some embodiments, the alarm data may also include daily exposure data, wherein, if the exposure data indicates that the level is near the threshold that would trigger an alarm, that data may be considered in the equation as well. As an example, maintenance data may include using equipment (gas detector) with a fault and may include one or more of the following indications: Old Unit erasable programmable read-only memory (EPROM), Old Sensor EPROM, Low battery, Expired Sensor, and Damaged Sensor. As an example, test data may include one or more of the following indications: Bump failed devices, Calibration failed devices, Calibration due devices, Zero Calibration test, Fresh Air test, Span test, Audio test (Peak and Minimum), and Vibrating Alarm test (if vibrator installed).

FIG. 1 illustrates an exemplary dashboard display that may be used to display the analyzed results from the system. The GHI for a specific site and/or for the overall workplace may be displayed. The testing results may also be displayed graphically, and the specific events may be shown.

Figure 2:
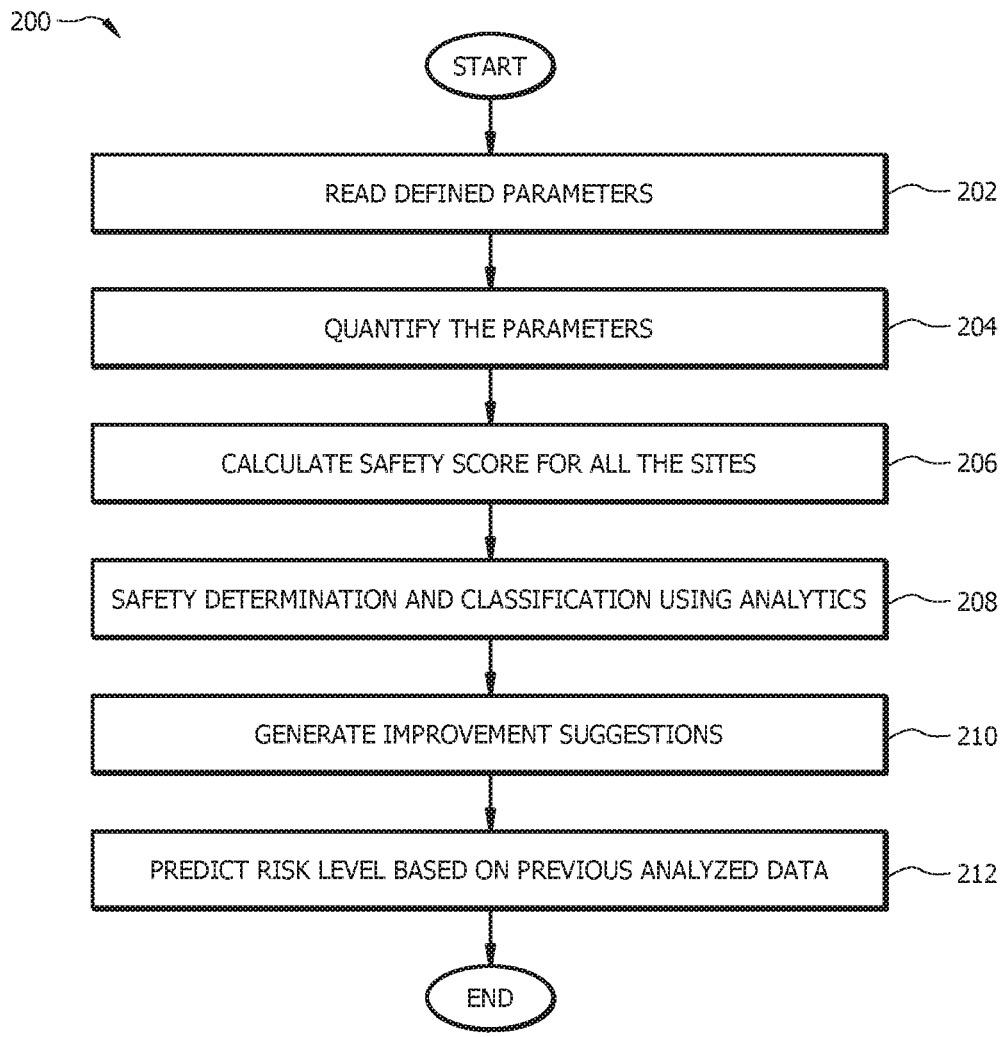
FIG. 2 illustrates a method for determining a safety benchmark for a workplace.

FIG. 2 illustrates an exemplary method 200 for determining a benchmark for a workplace. At step 202, defined parameters may be read by a corresponding sensor or testing device. These parameters may include alarm data, maintenance data, and/or test data, among other similar parameters related to gas detections that may be collected. At step 204, the parameters may be quantified and converted into a single numerical value for each category. At step 206, the quantified parameters may be processed using an equation to calculate a safety benchmark (GHI) for a particular site or area within a workplace. In some embodiments, these steps may be completed at a plurality of sites, and the sites may be averaged to determine a safety benchmark for the workplace. After the safety benchmark has been calculated, at step 208, the safety benchmark may be used to determine the safety level of a specific site, area, or workplace, and the determined safety benchmarks may be further analyzed. In some embodiments, at step 210, the analysis of the safety benchmarks for different sites or areas may be used to generate possible improvements for the sites that might improve the safety benchmark for that site.

In some embodiments, at step 212, the calculated GHI for a site may be used to predict a risk level for a site based on the prior exposure levels. This risk level may be used to determine if precautionary steps should be taken in a particular site to avoid exposure to hazardous gases. Additionally, the information and GHI from other sites may be used to predict possible hazards at a particular site. In some embodiments, faulty data may be identified and removed from the GHI calculation.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as comprises, includes, and having should be understood to provide support for narrower terms such as consisting of, consisting essentially of, and comprised substantially of. Use of the term "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A method for determining a safety benchmark for a workplace comprising:
   receiving alarm data from a plurality of gas detectors within the workplace;
   receiving test data from the plurality of gas detectors within the workplace;
   receiving maintenance data from the plurality of gas detectors within the workplace;
   determining a first quantified parameter for the alarm data;
   determining a second quantified parameter for the test data;
   determining a third quantified parameter for the maintenance data;
   calculating a gas health indicator (GHI) using the quantified parameters;
   comparing the GHIs for multiple sites within the workplace; and
   generating suggested improvements for the workplace based on the GHI and the data used to determine the GHI, and the comparison with other sites within the workplace.

2. The method of claim 1, wherein the GHI is calculated using the following equation: GHI=(Alarm data*A)+(Test data*B)+(Maintenance data*C), wherein A, B, and C are weighted variables.

3. The method of claim 1, wherein the GHI is calculated using the following equation: GHI=(Alarm data*6)+(Test data*3)+(Maintenance data*1).

4. The method of claim 1, wherein the alarm data comprises a normalized score that takes into account all of the alarm events that happen in an interval of time per the total number of gas detectors in use.

5. The method of claim 1, wherein the test data comprises a normalized score that takes into account all of the test failures that happen in an interval of time per total gas detectors in operation.

6. The method of claim 1, wherein the maintenance data comprises a normalized score that takes into account all of the maintenance failures that happen in an interval of time per the total number of gas detectors in use.

7. The method of claim 1, wherein alarm data comprises panic alarms, danger alarms, warning alarms, false alarms, short term exposure limit (STEL) alarms, and time weighted average (TWA) alarms.

8. The method of claim 1, wherein maintenance data comprises using a gas detector with a fault and includes one or more of the following indications: Old Unit erasable programmable read-only memory (EPROM), Old Sensor EPROM, Low battery, Expired Sensor, and Damaged Sensor.

9. The method of claim 1, wherein test data comprises one or more of the following indications: Bump failed devices, Calibration failed devices, Calibration due devices, Zero Calibration test, Fresh Air test, Span test, Audio test (Peak and Minimum), and Vibrating Alarm test (when vibrator installed).

10. The method of claim 1, further comprising predicting a risk level for a site based on the previously analyzed data, the GHI for the site, and the GHI for other sites in the workplace.

11. A method for determining a safety benchmark for a workplace comprising:
    receiving gas detector data from a plurality of gas detectors within the workplace;
    determining a first quantified parameter based on the received data;
    determining a second quantified parameter based on the received data;
    determining a third quantified parameter based on the received data;
    calculating a gas health indicator (GHI) using the quantified parameters using the following equation GHI= (first quantified parameter*A)+(second quantified parameter*B)+(third quantified parameter*C), wherein A, B, and C are weighted variables;
    comparing the GHIs for multiple sites within the workplace; and
    generating suggested improvements for the workplace based on the GHI and the data used to determine the GHI, and the comparison with other sites within the workplace.

12. The method of claim 11, wherein the first quantified parameter comprises alarm data and comprises a normalized score that takes into account all of the alarm events that happen in an interval of time per the total number of gas detectors in use.

13. The method of claim 12, wherein the second quantified parameter comprises test data and comprises a normalized score that takes into account all of the test failures that happen in an interval of time per total gas detectors in operation.

14. The method of claim 13, herein the third quantified parameter comprises maintenance data and comprises a normalized score that takes into account all of the maintenance failures that happen in an interval of time per the total number of gas detectors in use.

15. The method of claim 14, wherein A is greater than B, and wherein B is greater than C.

16. A method for determining a safety benchmark for a workplace comprising:
  receiving alarm data from a plurality of gas detectors within the workplace;
  receiving test data from the plurality of gas detectors within the workplace;
  receiving maintenance data from the plurality of gas detectors within the workplace;
  determining a first quantified parameter for the alarm data;
  determining a second quantified parameter for the test data;
  determining a third quantified parameter for the maintenance data;
  calculating a gas health indicator (GHI) using the quantified parameters using the following equation: GHI=(first quantified parameter*A)+(second quantified parameter*B)+(third quantified parameter*C), wherein A, B, and C are weighted variables;
  comparing the GHIs for multiple sites within the workplace;
  generating suggested improvements for the workplace based on the GHI and the data used to determine the GHI, and the comparison with other sites within the workplace; and
  predicting a risk level for a site based on the previously analyzed data, the GHI for the site, and the GHI for other sites in the workplace.

17. The method of claim 16, wherein the alarm data comprises a normalized score that takes into account all of the alarm events that happen in an interval of time per the total number of gas detectors in use.

18. The method of claim 16, wherein the test data comprises a normalized score that takes into account all of the test failures that happen in an interval of time per total gas detectors in operation.

19. The method of claim 16, wherein the maintenance data comprises a normalized score that takes into account all of the maintenance failures that happen in an interval of time per the total number of gas detectors in use.

20. The method of claim 16, further comprising identifying and removing faulty data from the calculation.

* * * * *